US012768782B2

(12) United States Patent
Dai et al.

(10) Patent No.: US 12,768,782 B2
(45) Date of Patent: Oct. 20, 2026

(54) OPTICAL SENSING DEVICE AND METHOD FOR MANUFACTURING THE SAME

(71) Applicant: Taiwan-Asia Semiconductor Corporation, Hsinchu City (TW)

(72) Inventors: Shu-Wen Dai, Hsinchu City (TW); Fu-Yung Tsai, Hsinchu City (TW)

(73) Assignee: TAIWAN-ASIA SEMICONDUCTOR CORPORATION, Hsinchu City (TW)

( * ) Notice: Subject to any disclaimer, the term of this patent is extended or adjusted under 35 U.S.C. 154(b) by 102 days.

(21) Appl. No.: 18/765,797

(22) Filed: Jul. 8, 2024

(65) Prior Publication Data

US 2025/0283812 A1 Sep. 11, 2025

(30) Foreign Application Priority Data

Mar. 5, 2024 (TW) ................................ 113107849

(51) Int. Cl.

| | |
|---|---|
| ***G01N 21/47*** | (2006.01) |
| ***G01N 21/359*** | (2014.01) |
| ***G01N 33/66*** | (2006.01) |

(52) U.S. Cl.

CPC ......... *G01N 21/474* (2013.01); *G01N 21/359* (2013.01); *G01N 33/66* (2013.01); *G01N 2201/06153* (2013.01)

(58) Field of Classification Search

CPC .... G01N 21/474; G01N 21/359; G01N 33/66; G01N 2201/06153; A61B 5/14532; A61B 5/1455

See application file for complete search history.

(56) References Cited

U.S. PATENT DOCUMENTS

| | | | | |
|---|---|---|---|---|
| 10,542,919 B2 * | 1/2020 | Xu | A61B 5/1455 | |
| 11,454,589 B2 * | 9/2022 | Benni | A61B 5/0075 | |
| 2005/0023489 A1 * | 2/2005 | Kikuchi | H10W 90/00 | 250/214 R |
| 2011/0300361 A1 * | 12/2011 | Nakayama | C09J 7/29 | 428/220 |
| 2020/0168757 A1 * | 5/2020 | Lin | G01J 3/10 | |
| 2024/0185800 A1 * | 6/2024 | Kawashima | A61B 5/1172 | |

FOREIGN PATENT DOCUMENTS

| | | |
|---|---|---|
| CN | 104523368 A | 4/2015 |
| CN | 107710056 A | 2/2018 |
| CN | 105266773 B | 7/2018 |

(Continued)

OTHER PUBLICATIONS

A Office Action and Search Report for TW Application No. 113107849 dated May 7, 2025 is attached (10 pages).

*Primary Examiner* — Seung C Sohn

(74) *Attorney, Agent, or Firm* — MUNCY, GEISSLER, OLDS & LOWE, P.C.

(57) ABSTRACT

A light-sensing device and a manufacturing method thereof are provided. The light-sensing device includes a substrate, at least one light-emitting component and a light-sensing component. The light-emitting component is used to emit a light, and the light-sensing component is used to receive the diffuse-reflected light after the light is diffuse-reflected by an external object. Moreover, the light-emitting component and the light-sensing component are individually and separately mounted on the substrate.

13 Claims, 8 Drawing Sheets

(56) References Cited

FOREIGN PATENT DOCUMENTS

| | | | |
|---|---|---|---|
| CN | 111214209 | A | 6/2020 |
| CN | 215959856 | U | 3/2022 |
| EP | 2989975 | B1 | 6/2018 |
| TW | 201825048 | A | 7/2018 |
| TW | 202112307 | A | 4/2021 |
| TW | I829489 | B | 1/2024 |

* cited by examiner

OPTICAL SENSING DEVICE AND METHOD FOR MANUFACTURING THE SAME

CROSS-REFERENCES TO RELATED APPLICATIONS

This application claims priority to Taiwan Patent Application No. 113107849 filed on Mar. 5, 2024, which is hereby incorporated by reference in its entirety.

BACKGROUND OF THE INVENTION

Field of the Invention

The present invention relates to a light-sensing device and a method for manufacturing the same, in particular, a light-sensing device with multiple combinations of flexibility and measurement accuracy and a manufacturing method thereof.

Descriptions of the Related Art

Non-invasive blood glucose testing is a technology that measures blood glucose levels without puncturing the skin or taking a blood sample. Such technology has important application values in reducing the inconvenience of diabetic patients and improving the frequency and convenience of blood glucose monitoring. Near-infrared spectroscopy (NIRS) blood glucose detection technology is a non-invasive optical blood glucose detection technology which utilize near-infrared light with a wavelength ranges from 700 nanometers (nm) to 2500 nanometers (nm). The infrared light in this wavelength range can be absorbed and scattered by components such as water, fat, and protein in tissues. This technology is used to presume the blood sugar concentration in human tissues by measuring the changes in absorption, reflection and scattering of human tissues before and after infrared light is irradiated to human tissues.

As shown in FIG. 1, which shows a schematic cross-sectional view of a conventional near-infrared blood glucose detection device 1. A conventional blood glucose detection device is usually a multi-chip module 10. When manufacturing a multi-chip module, several light-sensing components and several light-emitting components are solidified onto a common conductive substrate. After that, several multi-chip modules are formed through processes such as wire bonding, film pasting, light-blocking component production, and cutting. Then, the multi-chip module 10 is mounted on a printed circuit board 20 to finish the whole process. Each multi-chip module 10 includes a light-sensing component 11 and a plurality of light-emitting components 12 which are bonded on a conductive substrate 13. This is a design of a light-blocking component 14 arranged between each light-sensing component 11 and the light-emitting components 12.

The light-blocking component 14 of the conventional blood glucose detection device 1 shown in FIG. 1 is designed as a half-cut and glue-dispensing structure. After the above-mentioned multi-chip module 10 has been processed by the packaging process of the protective layer 15 and the optical film cover 16, and then cuts the package body between the light-emitting component and the light-sensing component in a half-cutting manner to form a trench for the intended light-blocking component. The grooves are then filled with glue to form the light-blocking component 14. One of the shortcomings of the conventional blood glucose detection device 1 is that the light-blocking component 14 only exists between the light-sensing component 11 and the light-emitting component 12 and can only block the light transmission between the light-sensing component and the light-emitting component. There is no light-blocking component design around the multi-chip module 10 so it cannot block the entry of ambient light from the outside, and it cannot prevent the light-emitting components from leaking to unintended external environments. Moreover, the above-mentioned conventional half-cutting and dispensing processes also have shortcomings such as complicated process, low yield, slow production, and high cost.

In addition, when manufacturing a multi-chip module, several light-sensing components and several light-emitting components are bonded on a common conductive substrate. The configuration of each chip in the multi-chip module formed after wire bonding, cutting and other processes has been fixed. At this time, if any chip is detected to be defective during the manufacturing process, any chip in the multi-chip module cannot be replaced. The entire module can only be discarded and there is no possibility of replacement.

Please refer to FIG. 2A and FIG. 2B together, which shows that the multi-chip module 10 in the conventional blood glucose detection device may be worn too loosely or too tightly due to the difference in the user's operation status and the user's human tissue. As shown in FIG. 2A, if the gap between the blood glucose detection device and human tissue is too loose, the multi-chip module 10 may suffer from optical signal loss. On the other hand, as shown in FIG. 2B, if the gap between the blood glucose detection device and the human tissue is too tight, the multi-chip module 10 will excessively press the human tissue and will force the glucose 30 in the human tissue to be expelled outward to other locations inside the human tissue. Accordingly, the blood glucose concentration near the measured area will decrease, and indirectly, the measurement results will be distorted and measurement accuracy will be affected. In order to overcome the above problems, the industry urgently needs an innovative blood glucose detection device and its manufacturing method to improve the above problems.

SUMMARY OF THE INVENTION

The main purpose of the present invention is to provide an innovative light-sensing device and its manufacturing method to improve the following problems of the conventional technology. First, the manufacturing process is complicated, low yield, slow production, and high cost. Second, the module configuration is fixed and the flexibility of change is small. Third, it is impossible to accurately interpret the signal and the measurement accuracy will be influenced.

To achieve the above objective, the present invention discloses a light-sensing device which includes a substrate, at least one light-emitting component and a light-sensing component. The light-emitting component is used to emit a light, and the light-sensing component is used to receive the diffuse-reflected light after the light is diffuse-reflected by an external object. Moreover, the light-emitting component and the light-sensing component are individually and separately mounted on the substrate.

In one embodiment of the light-sensing device of the present invention, the light-sensing device further includes at least one light-blocking component surrounding the at least one light-emitting component and the light-sensing component to block the light emitted by the at least one light-emitting component from leaking out of the light-sensing device and also block an ambient light and the light from being directly received by the light-sensing component without reflection.

In one embodiment of the light-sensing device of the present invention, the material of the at least one light-blocking component is selected from one of the group consisting of thermoplastic polymers, carbon fiber materials, ceramic materials, and their combinations.

In one embodiment of the light-sensing device of the present invention, the transmittance rate of the at least one light-blocking component is not greater than 5%.

In one embodiment of the light-sensing device of the present invention, the reflection rate of the at least one light-blocking component is not less than 95%.

In one embodiment of the light-sensing device of the present invention, the light-sensing device further includes a pressure-sensitive component disposed on the at least one light-blocking component for sensing an external force exerted on the light-sensing device.

In one embodiment of the light-sensing device of the present invention, the external force sensed by the pressure-sensitive component and applied to the light-sensing device is less than 100 Newtons (N).

In one embodiment of the light-sensing device of the present invention, the light-sensing device further includes an optical film plate covering the light-sensing component for selectively allowing only light of a specific wavelength to pass through and blocking light of other wavelengths from passing through.

To achieve the above objective, the present invention discloses a method of manufacturing a light-sensing device which includes: providing a substrate, providing at least one light-emitting component, and providing a light-sensing component, and mounting the at least one light-emitting component and the light-sensing component to the substrate individually and separately, wherein the light-sensing component is used to receive a diffuse-reflected light after the light is diffuse-reflected by an external object.

In one embodiment of the method of manufacturing a light-sensing device of the present invention, the method further includes a step of providing a least one light-blocking component surrounding the at least one light-emitting component and the light-sensing component to block the light emitted by the at least one light-emitting component from leaking out of the light-sensing device and also block an ambient light and the light from being directly received by the light-sensing component without reflection.

In one embodiment of the method of manufacturing a light-sensing device of the present invention, the method further includes a step of providing a pressure-sensitive component disposed on the at least one light-blocking component for sensing an external force exerted on the light-sensing device.

In one embodiment of the method of manufacturing a light-sensing device of the present invention, wherein the step of providing at least one light-emitting component and a light-sensing component is the step of: mounting the at least one light-emitting component and the light-sensing component to a conductive substrate, providing a protective layer to cover the at least one light-emitting component and the light-sensing component, and cutting the conductive substrate to form the at least one light-emitting component and the light-sensing component individually and separately.

In one embodiment of the method of manufacturing a light-sensing device of the present invention, the method further includes a step of providing an optical film cover to cover the protective layer and then cutting the conductive substrate.

After reviewing the diagrams and the subsequent descriptions of the embodiments, those skilled in the art will readily understand other objectives of the present invention, as well as the technical means and embodiments thereof.

DETAILED DESCRIPTION OF THE PREFERRED EMBODIMENT

The content of the present invention will be explained through examples. The embodiments of the present invention are not intended to limit the invention to any particular environment, application, or specific method as described in the examples. Therefore, the description of the embodiments is only intended to elucidate the objectives of the present invention and not to limit the invention. It should be noted that in the following embodiments and diagrams, devices not directly related to the present invention have been omitted and not depicted. Additionally, the dimensional relationships between devices in the diagrams are for ease of understanding and are not intended to limit the actual proportions.

Figure 1:
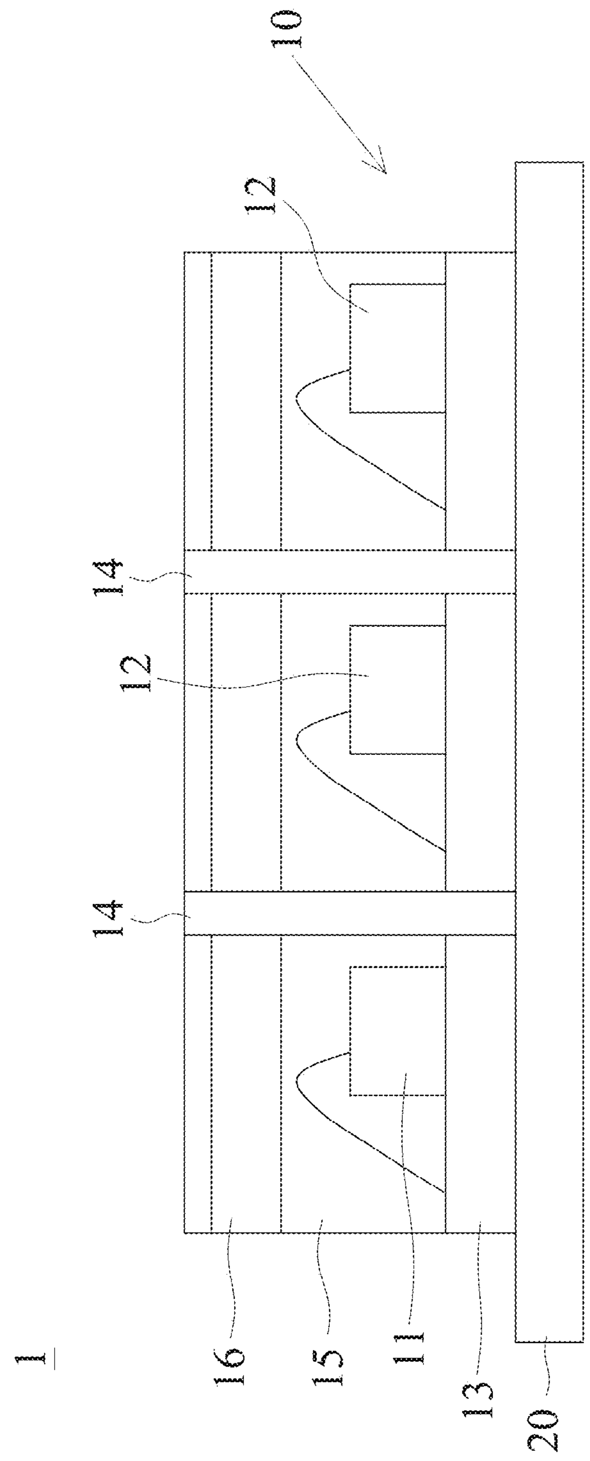
FIG. 1 depicts a schematic cross-sectional view of a conventional near-infrared blood glucose detection device.
Figure 2A:
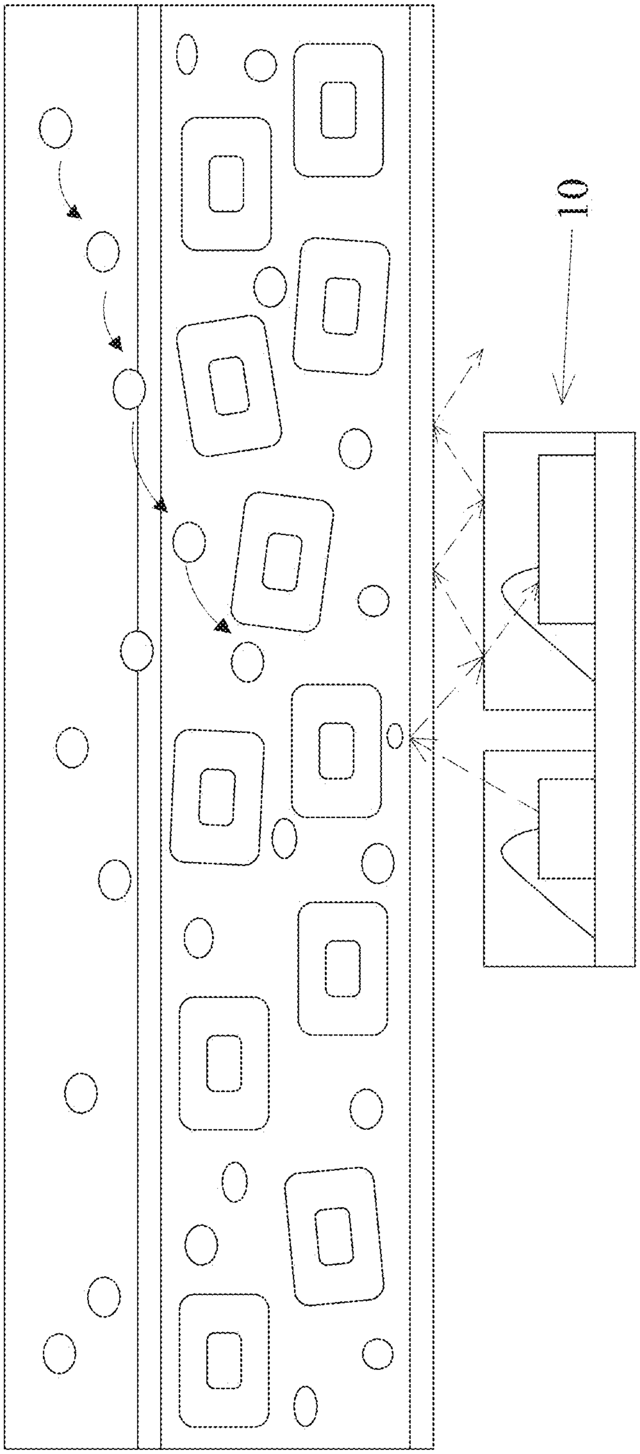
FIG. 2A and FIG. 2B illustrate schematic diagrams of the multi-chip module in the conventional blood glucose detection device due to the user wearing too loosely or too tightly.
Figure 2B:
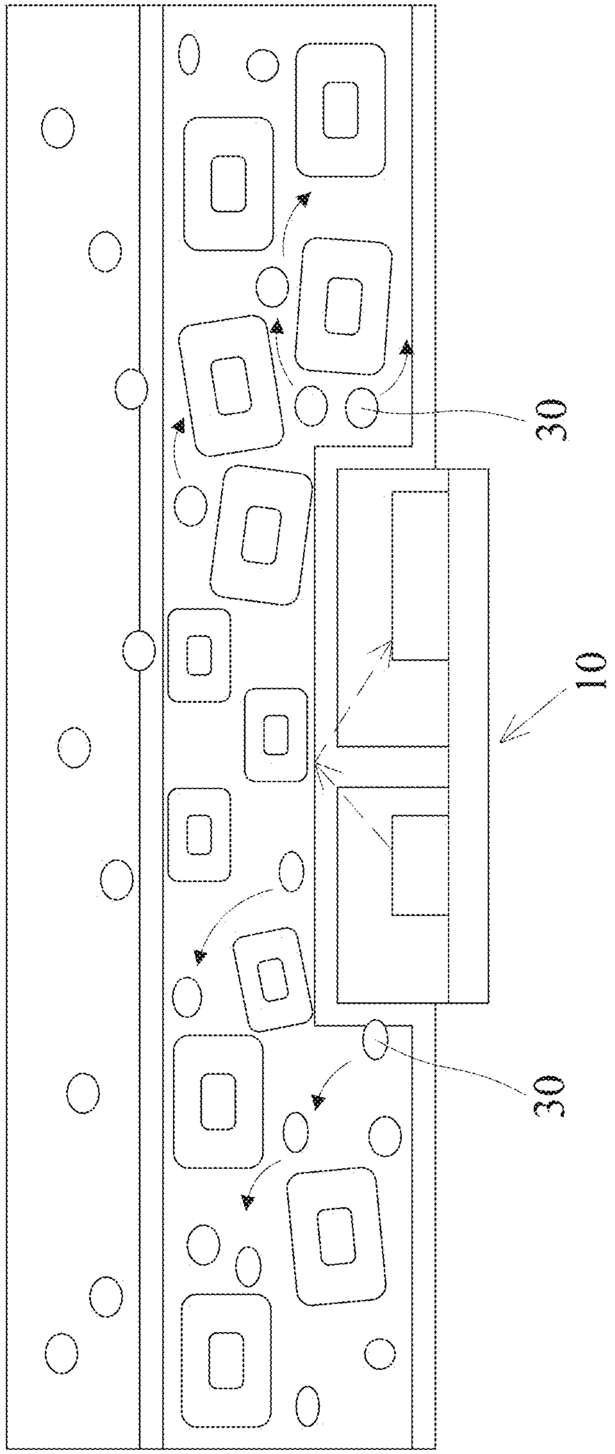
Figure 3:
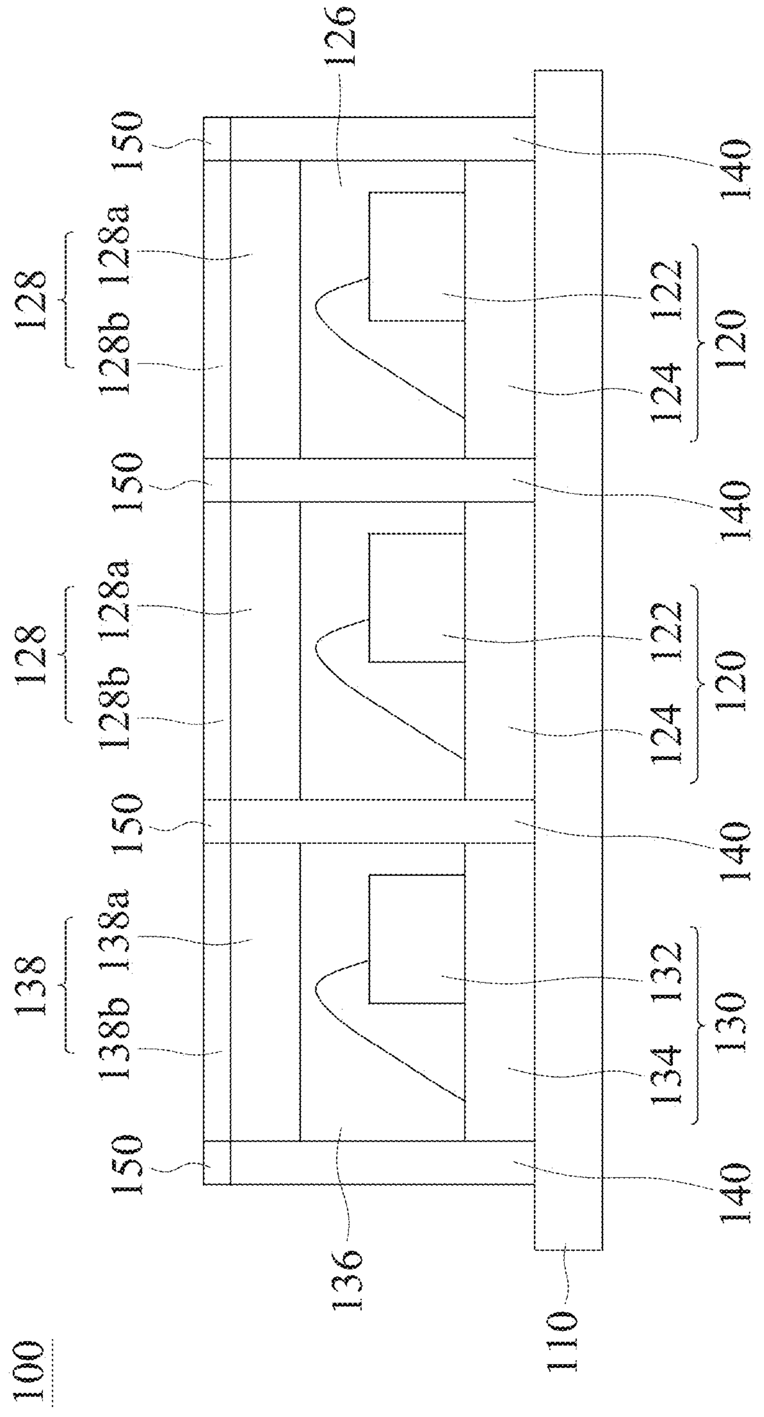
FIG. 3 illustrates a structural schematic diagram of a light-sensing device in one embodiment of the present invention.

Please refer to FIG. 3, which illustrates a schematic diagram of a light-sensing device in one embodiment of the present invention. One of the differences between the light-sensing device of the present invention and the conventional device is that the present invention utilizes a single-chip module instead of the multi-chip module used in the conventional device. Both the light-emitting component providing the light source and the light-sensing component generating electrical signals from the received light are independently designed as single-chip modules in the structure aiming to enhance the flexibility of module configuration and the possibility of replacing defective modules during manufacturing production. Further details are described below.

As shown in FIG. 3, the light-sensing device 100 of the present invention comprises a substrate 110, two light-emitting components 120, a light-sensing component 130, and several light-blocking components 140. Each light-emitting component 120 includes a light-emitting diode (LED) chip 122 and a conductive substrate 124. The LED chip 122 is mounted on the conductive substrate 124 and electrically connected to it. The LED chip 122 is used to emit light of a specific wavelength. In the specific application of glucose concentration detection, the LED chip 122 can emit near-infrared light with wavelengths ranging from 700 nanometers (nm) to 2500 nm. In other embodiments, different LED chips emitting different wavelengths can be used according to different detection requirements. It should be noted that each light-emitting component 120 further includes a protective layer 126 covering the LED chip 122 to protect it and form a light-emitting package. Additionally, in the embodiment shown in FIG. 3, each light-emitting component 120 further includes an optical film plate 128 covering the protective layer 126 and the LED chip 122, wherein the optical film plate 128 comprises a glass cover plate 128*a* and an optical coating 128*b*.

Furthermore, the light-sensing component 130 comprises a light-sensing chip 132 and a conductive substrate 134. The light-sensing chip 132 is mounted on the conductive substrate 134 and electrically connected to it. The light emitted by the light-emitting component 120 is diffusely reflected by an external object, such as human tissue. The diffusely reflected light is received by the light-sensing chip 132 of the light-sensing component 130, which generates a corresponding electrical signal based on it. After conversion by the system, the corresponding blood glucose concentration within, for example, human tissue is obtained. Similarly, the light-sensing component 130 also includes a protective layer 136 covering the light-sensing chip 132 to protect it and form a light-sensing package. Additionally, the light-sensing component 130 includes an optical film plate 138 covering the protective layer 136 and the light-sensing chip 132, wherein the optical film plate 138 comprises a glass cover plate 138*a* and an optical coating 138*b*. It should be noted that this optical film plate 138 can be an optical filter, such as a bandpass filter (BPF), used to selectively allow only light within a specific wavelength range to pass through while blocking or attenuating light of other wavelengths.

Moreover, unlike the prior art, the light-emitting component 120 and the light-sensing component 130 in the present invention are separate and distinct components. They are individually and separately installed on a substrate 110 with printed circuits during the subsequent production process of the light-sensing device 100. Therefore, different numbers of light-emitting components 120 and light-sensing components 130 can be installed according to the different final requirements of the light-sensing device 100, providing flexibility in product configuration. Furthermore, even when one of the components is defective, the light-sensing device 100 of the present invention still offers the possibility of replacing the faulty components on the substrate 110. Detailed explanations regarding this aspect can be provided in the subsequent description of the manufacturing method for the light-sensing device 100 of the present invention.

Figure 4:
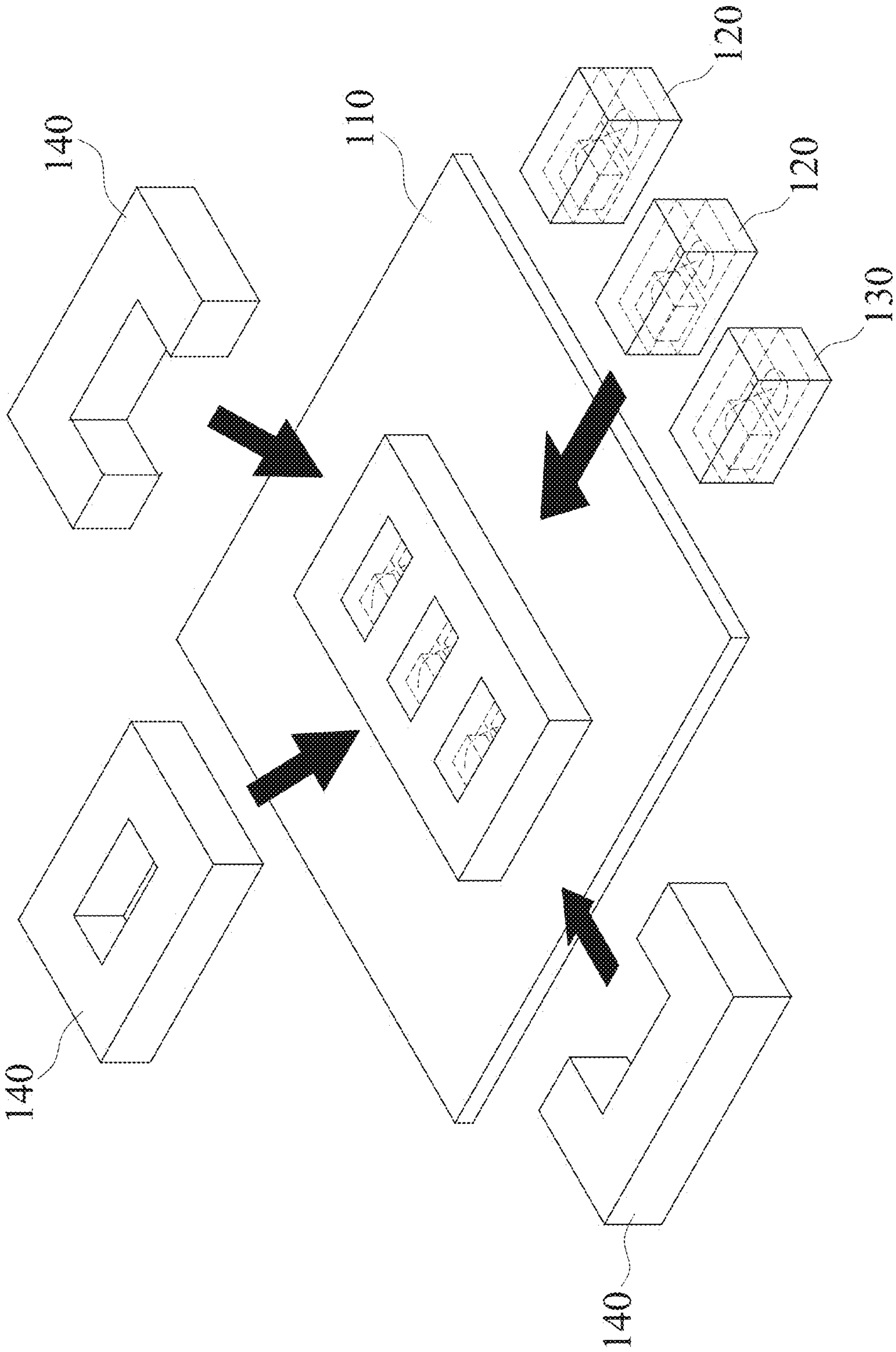
FIG. 4 illustrates a schematic diagram of the combination of light-emitting components, light-sensing components, and light-blocking components in one embodiment of the present invention.

Continuing with reference to FIG. 3, another difference between the present invention and the prior art lies in the inclusion of at least one light-blocking component 140 in the present invention's light-sensing device 100. This component surrounds the light-emitting component 120 and the light-sensing component 130 to prevent light emitted by the light-emitting component 120 from leaking outside the light-sensing device 100. It also blocks ambient light and prevents light that has not been reflected by external objects (such as human tissue) from being directly received by the light-sensing component 130. Specifically, please refer to FIG. 4, which shows that the shape of the light-blocking component can be designed in different forms according to requirements, such as, but not limited to, an "O" shaped or a "C" shaped structure. In the embodiment shown in FIG. 4, an "O" shaped light-blocking component 140 and two "C" shaped light-blocking components 140 are used to enclose two light-emitting components 120 and one light-sensing component 130 entirely for achieving the aforementioned purpose of preventing light leakage and blocking ambient light and specific wavelength light from entering the light-sensing component 130. The height of the light-blocking component 140 can be, but is not limited to, greater than or equal to 0.4 millimeters (mm), and its width is not less than 0.1 millimeters (mm). Furthermore, the material composing the light-blocking component 140 can be selected from one or a combination of thermoplastic polymers, carbon fiber materials, ceramic materials, among which the thermoplastic polymers may include polystyrene, low-density polyethylene, polyacetal, polylactic acid, acrylonitrile-butadiene-styrene copolymer, etc. Additionally, the transmittance rate of the material constituting the light-blocking component should not exceed 5%, or the reflection rate should not be less than 95% to achieve the effectiveness of blocking light.

In a preferred embodiment of the present invention, to avoid problems arising from differences in user operation status during the actual application of the light-sensing device and the occurrence of loose or tight wearing conditions between the user's body tissue and the device, the light-sensing device 100 of the present invention further includes a pressure-sensitive component 150. This component can be adhered to the contour above the light-blocking component 140 and is placed on the light-blocking component 140 to sense the external force applied to the light-sensing device 100. Specifically, when the light-sensing device 100 is worn too loosely against the body tissue, the pressure-sensitive component 150 may sense zero external force applied to the light-sensing device 100 or approach zero. At this point, the light-sensing device 100 can emit a warning signal indicating loose wearing, for reminding the user to readjust the wearing state. On the other hand, when the light-sensing device 100 is worn too tightly against the body tissue causing the pressure-sensitive component 150 to sense an external force exceeding the preset value of the system, for example, it could be 100 Newtons (N), the light-sensing device 100 can emit a corresponding warning indicating tight wearing for reminding the user to readjust the wearing state to obtain accurate measurement values, such as blood glucose concentration.

Figure 5:
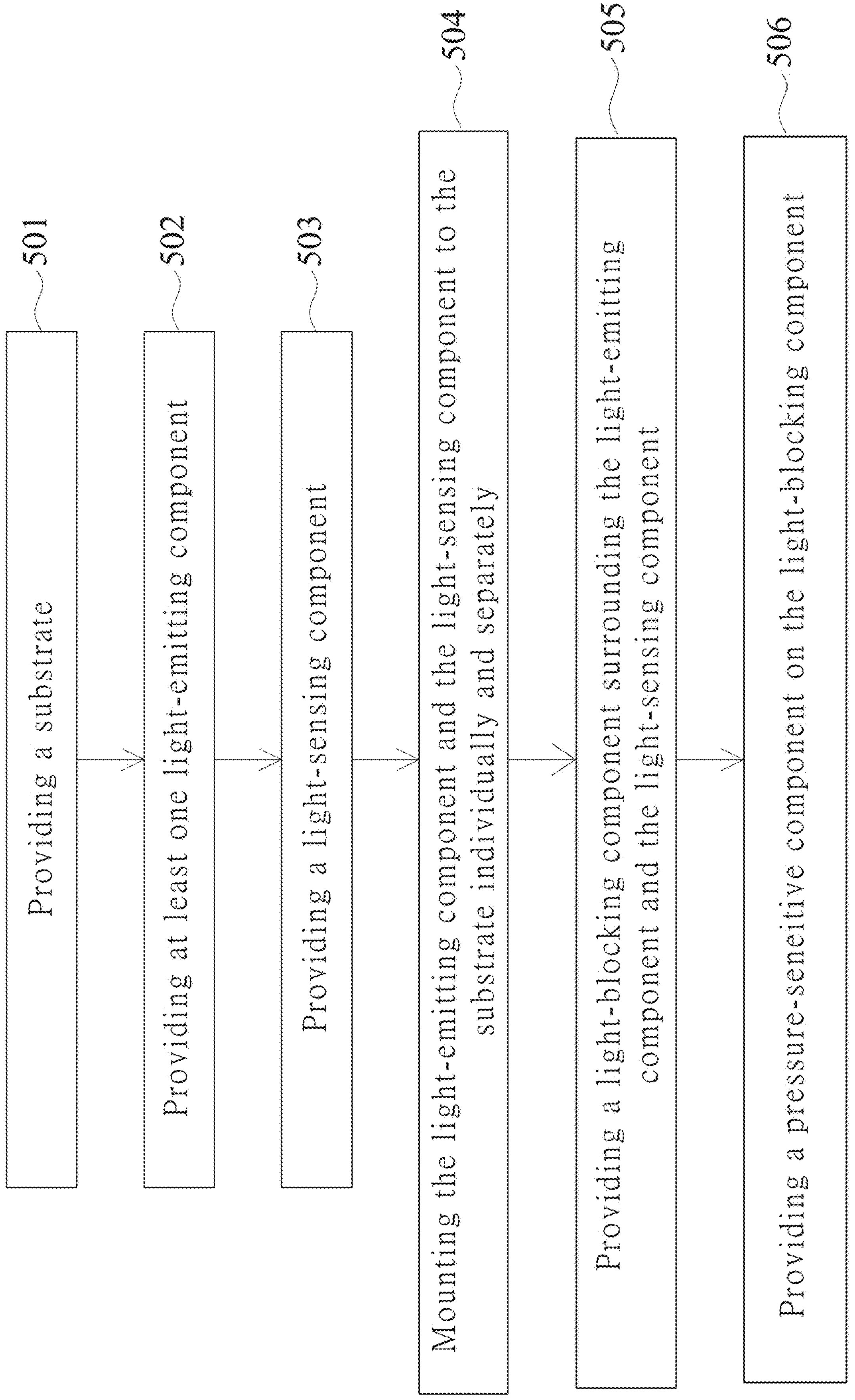
FIG. 5 depicts a flowchart of manufacturing a light-sensing device in one embodiment of the present invention.

Please refer to FIG. 5, which illustrates a flowchart of the process for manufacturing the light-sensing device according to the present invention. In step 501, a substrate containing printed circuits is provided. In step 502, at least one light-emitting component is provided according to the requirements of the light-sensing device to emit light in a specific wavelength range. In step 503, a light-sensing component is provided according to the requirements of the light-sensing device to receive the diffuse light reflected by external objects from the light emitted by the light-emitting component. In step 504, a specific number of individual and separate light-emitting components and light-sensing components are installed on the substrate according to the requirements of the light-sensing device. In step 505, a specific number of light-blocking components are provided according to the requirements of the light-sensing device to surround the above-mentioned light-emitting components and light-sensing components for blocking the light emitted by the light-emitting components from leaking outside the light-sensing device, and also blocking ambient light and the light not reflected by external objects from being directly received by the light-sensing components. In step 506, a pressure-sensitive component is provided and placed on the light-blocking component to sense the external force applied to the light-sensing device.

Figure 6:
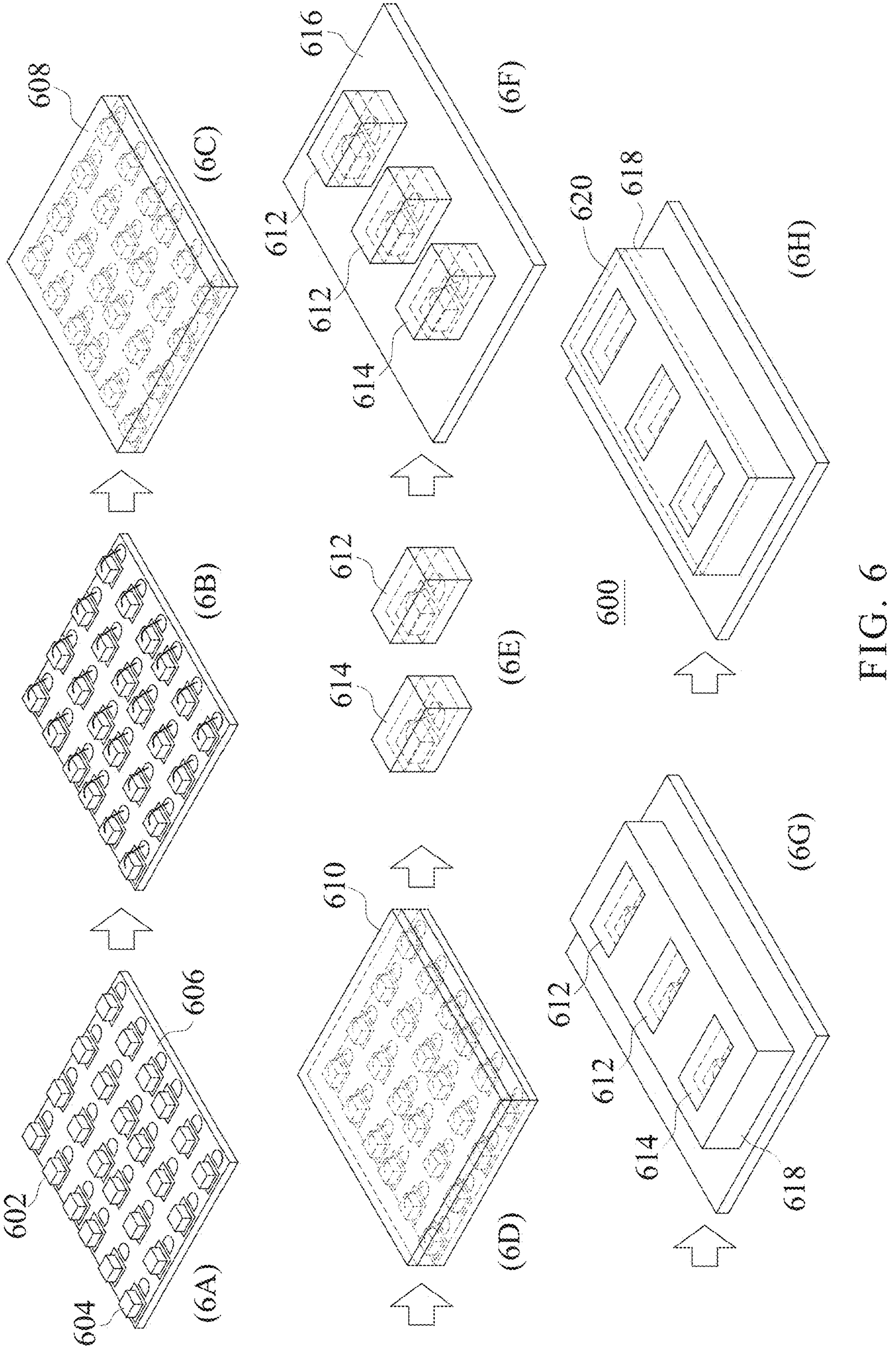
FIG. 6 illustrates a schematic diagram of manufacturing light-emitting components and light-sensing components in one embodiment of the present invention.

The following will describe how the present invention manufactures individual and separate light-emitting components and light-sensing components in a light-sensing device of two embodiments. Please refer to FIG. 6. In Process 6A, several light-emitting diode chips 602 and several light-sensing chips 604 fixed on a conductive substrate 606 by die bonding or surface adhesive technology are shown. Next, in Process 6B, wire bonding is performed to electrically connect the light-emitting diode chips 602 and the light-sensing chips 604 to the conductive substrate 606. Subsequently, in Process 6C, a protective layer 608 is formed by a molding process to cover the light-emitting diode chips 602 and the light-sensing chips 604. Then, in Process 6D, an optical thin film cover plate 610 with optical thin films is provided to cover the protective layer 608, simultaneously covering the light-emitting diode chips 602 and the light-sensing chips 604. Next, in Process 6E, the conductive substrate 606 is cut using cutting equipment to form individual and separated, fully encapsulated light-emitting components 612 and light-sensing components 614. Then, in Process 6F, according to the design requirements of the light-sensing device, a certain number of individual and separated light-emitting components 612 and light-sensing components 614 are assembled onto a printed circuit board 616. In Process 6G, a suitable number and structural design of light-blocking components 618 are used to cover the entire periphery of the light-emitting components 612 and light-sensing components 614. Finally, in Process 6H, a pressure-sensitive component 620 is adhered to the assembled light-blocking component 618 so the light-sensing device 600 of the present invention has been done.

Figure 7:
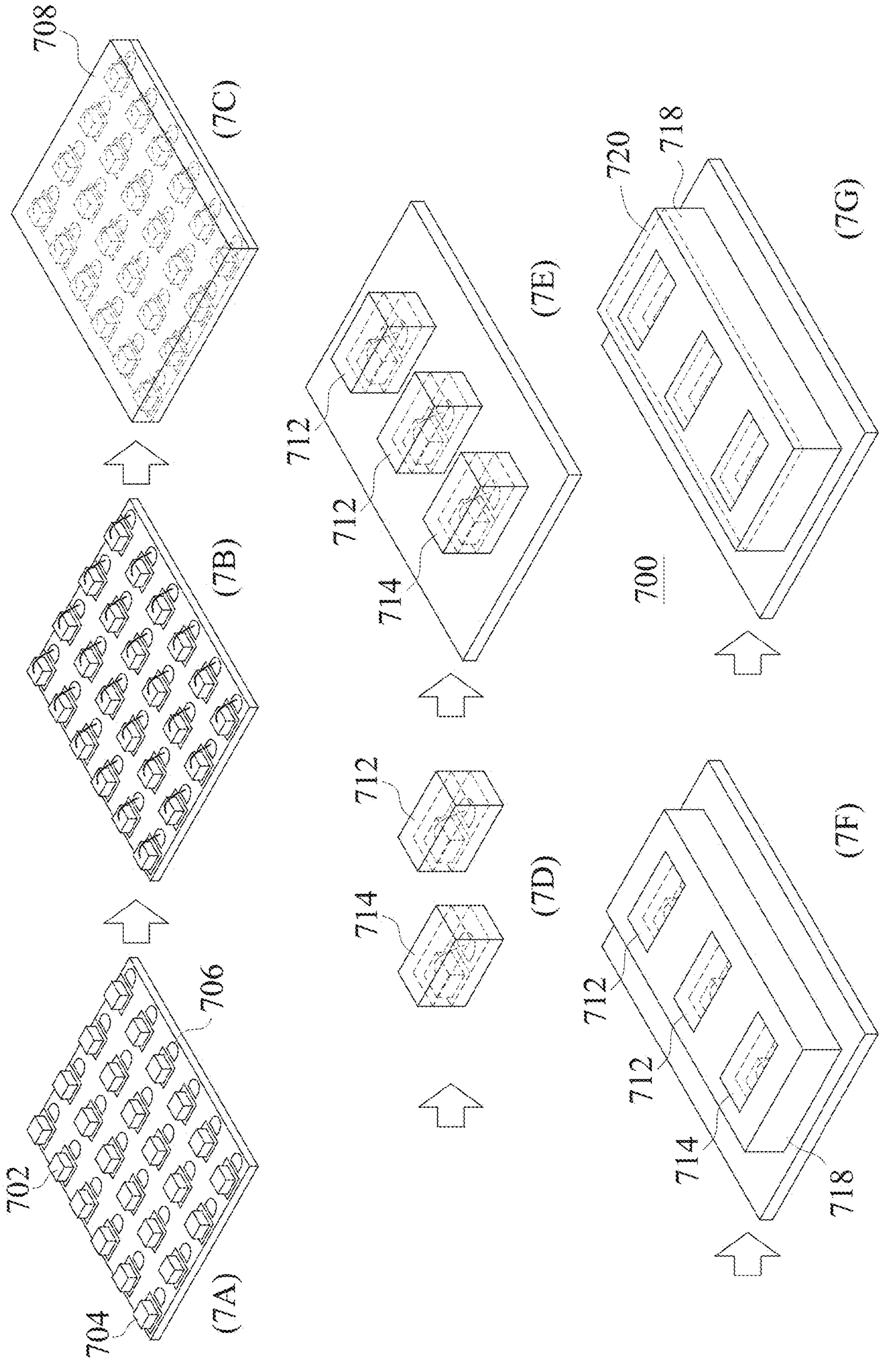
FIG. 7 shows a schematic diagram of manufacturing light-emitting components and light-sensing components in another embodiment of the present invention.

Please refer to FIG. 7, which illustrates another embodiment of how the present invention manufactures individual and separate light-emitting components and light-sensing components. First, similarly, in Process 7A, several light-emitting diode chips 702 and several light-sensing chips 704 are fixed onto a conductive substrate 706 using die bonding or surface adhesive technology. However, unlike the previous embodiment, the surface of the light-sensing chips 704 in this embodiment is already attached with an optical thin film, which can filter out light in a specific wavelength range from being received by the light-sensing chips 704. Therefore, the subsequent process of attaching an optical thin film cover plate can be saved. Next, in Process 7B, wire bonding is performed to electrically connect the light-emitting diode chips 702 and the light-sensing chips 704 to the conductive substrate 706. Subsequently, in Process 7C, a protective layer 708 is formed by a molding process to cover the light-emitting diode chips 702 and the light-sensing chips 704. Then, in Process 7D, the conductive substrate 706 is cut using cutting equipment to form individual and separate, fully encapsulated light-emitting components 712 and light-sensing components 714. Next, in Process 7E, according to the design requirements of the light-sensing device, a certain number of individual and separate light-emitting components 712 and light-sensing components 714 are assembled onto a printed circuit board 716. In Process 7F, a light-blocking component 718 is used to cover the entire periphery of the light-emitting components 712 and light-sensing components 714. Finally, in Process 7G, a pressure-sensitive component 720 is adhered to the assembled light-blocking component 718 to complete the light-sensing device 700 of the present invention.

As mentioned above, the application of "single-chip module" pattern for light-emitting components and light-sensing components in the present invention allows for the selection of different numbers of module components according to the requirements of different applications, and with different structural shapes, such as modular light-blocking components in "O" shaped or "C" shaped designs. These components can be freely combined on a printed circuit board for providing flexibility in diverse combinations without limitations on the quantity, position, or arrangement thereof. Moreover, if any module is defective, the light-sensing device of the present invention offers the possibility of replacing it with a good one. It is not necessary to discard the entire module as the traditional manner. Therefore, the light-sensing device of the present invention can address the drawbacks of traditional multi-chip module glucose monitoring devices. The modified design can: (1) improve light-blocking efficiency due to a complete light-blocking component design, (2) enhance module yield by replacing defective products, (3) increase production speed with single-chip module design, (4) reduce overall device production costs with single-chip module design flexibility, and (5) provide diverse choices to meet user needs with increased module matching flexibility. Particularly, the light-sensing device of the present invention features a pressure-sensitive component that provides force sensing functionality for enabling the non-invasive glucose monitoring module of the present invention to screen or calibrate measurement data. Thereby, glucose monitoring accuracy will be enhanced.

The above embodiments are essentially for illustrative purposes only and are not intended to limit the embodiments of the claims or the applications or uses thereof. Furthermore, although at least one exemplary embodiment has been presented in the foregoing embodiments, it should be understood that the present invention may have numerous variations. It should also be understood that the embodiments described herein are not intended to limit the scope, applications, or configurations of the claimed subject matter in any way. On the contrary, the foregoing embodiments may provide a convenient guide for those skilled in the art to implement one or more embodiments disclosed herein. Additionally, various changes may be made to the functions and arrangements of the components without departing from the scope defined by the claims, and the claims encompass all known equivalents and foreseeable equivalents at the time of filing of the present patent application.

What is claimed is:

1. A light-sensing device, including:

a main substrate;

at least one light-emitting component, having a first conductive substrate and a light-emitting chip mounted on the first conductive substrate, the at least one light-emitting component configured to emit a light; and a light-sensing component, having a second conductive substrate and a light-sensing chip mounted on the second conductive substrate, the light-sensing component configured to receive a diffuse-reflected light after the light is diffuse-reflected by an external object, wherein the at least one light-emitting component and the light-sensing component are individually and separately mounted on the main substrate via the first conductive substrate and the second conductive substrate, respectively.

2. The light-sensing device of claim 1, further including at least one light-blocking component surrounding the at least one light-emitting component and the light-sensing component to block the light emitted by the at least one light-emitting component from leaking out of the light-sensing device and also block an ambient light and the light from being directly received by the light-sensing component without being diffuse-reflected.

3. The light-sensing device of claim 2, wherein the material of the at least one light-blocking component is selected from one of the group consisting of thermoplastic polymers, carbon fiber materials, ceramic materials, and their combinations.

4. The light-sensing device of claim 2, wherein the transmittance rate of the at least one light-blocking component is not greater than 5%.

5. The light-sensing device of claim 2, wherein the reflection rate of the at least one light-blocking component is not less than 95%.

6. The light-sensing device of claim 2, further including a pressure-sensitive component disposed on the at least one light-blocking component for sensing an external force exerted on the light-sensing device.

7. The light-sensing device of claim 6, wherein the external force sensed by the pressure-sensitive component and applied to the light-sensing device is less than 100 Newtons (N).

8. The light-sensing device of claim 1, further including an optical film plate covering the light-sensing component for selectively allowing only light of a specific wavelength to pass through and blocking light of other wavelengths from passing through.

9. A method of manufacturing a light-sensing device, including:

providing a main substrate;

providing at least one light-emitting component, the at least one light-emitting component having a first conductive substrate and a light-emitting chip mounted on the first conductive substrate, the at least one light-emitting component configured to emit a light;

providing a light-sensing component, the light-sensing component having a second conductive substrate and a light-sensing chip mounted on the second conductive substrate; and mounting the at least one light-emitting component and the light-sensing component to the main substrate individually and separately via the first conductive substrate and the second conductive substrate, respectively, wherein the light-sensing component is configured to receive a diffuse-reflected light after the light is diffuse-reflected by an external object.

10. The method of manufacturing a light-sensing device of claim 9, further including a step of providing a least one light-blocking component surrounding the at least one light-emitting component and the light-sensing component to block the light emitted by the at least one light-emitting component from leaking out of the light-sensing device and also block an ambient light and the light from being directly received by the light-sensing component without reflection.

11. The method of manufacturing a light-sensing device of claim 10, further including a step of providing a pressure-sensitive component disposed on the at least one light-blocking component for sensing an external force exerted on the light-sensing device.

12. The method of manufacturing a light-sensing device of claim 9, wherein the step of providing at least one light-emitting component and a light-sensing component is the step of:

mounting the at least one light-emitting component and the light-sensing component to a conductive substrate, providing a protective layer to cover the at least one light-emitting component and the light-sensing component, and cutting the conductive substrate to form the first conductive substrate of the at least one light-emitting component and the second conductive substrate of the light-sensing component individually and separately.

13. The method of manufacturing a light-sensing device of claim 12, further including a step of providing an optical film cover to cover the protective layer and then cutting the conductive substrate.

* * * * *